United States Patent
Mosher

(10) Patent No.: US 8,128,949 B2
(45) Date of Patent: Mar. 6, 2012

(54) KIT FOR INSECT BITES

(76) Inventor: John Mosher, Nanuet, NY (US)

( * ) Notice: Subject to any disclaimer, the term of this patent is extended or adjusted under 35 U.S.C. 154(b) by 967 days.

(21) Appl. No.: 12/082,624

(22) Filed: Apr. 14, 2008

(65) Prior Publication Data

US 2009/0258044 A1    Oct. 15, 2009

(51) Int. Cl.
    *A01N 25/32* (2006.01)
(52) U.S. Cl. .................. 424/406; 424/405; 424/408
(58) Field of Classification Search .................. None
    See application file for complete search history.

(56) References Cited

U.S. PATENT DOCUMENTS

| | | | | |
|---|---|---|---|---|
| 2,826,297 | A * | 3/1958 | Hein, Jr. | 206/572 |
| 3,739,961 | A * | 6/1973 | Soukeras | 224/579 |
| 3,868,015 | A * | 2/1975 | Thompson | 206/229 |
| 5,017,361 | A | 5/1991 | Powell, Jr. | |
| 5,702,709 | A | 12/1997 | Schulz | |
| 5,840,320 | A * | 11/1998 | Odom | 424/401 |
| 5,888,520 | A | 3/1999 | Toma | |
| 6,110,475 | A | 8/2000 | Toma | |
| 6,248,343 | B1 | 6/2001 | Jampani | |
| 6,248,763 | B1 | 6/2001 | Scivoletto | |
| 6,551,607 | B1 | 4/2003 | Minerath, III | |
| 7,026,319 | B1 | 4/2006 | Valletta | |
| 7,115,286 | B2 * | 10/2006 | Meredith | 424/725 |
| 7,691,419 | B2 * | 4/2010 | DiLeva | 424/725 |
| 2006/0171936 | A1 | 8/2006 | Gueniche | |
| 2006/0178368 | A1 | 8/2006 | Valletta | |

FOREIGN PATENT DOCUMENTS

WO    WO 2005/004598 A2    1/2005

* cited by examiner

*Primary Examiner* — Johann Richter
*Assistant Examiner* — Daniel L Branson
(74) *Attorney, Agent, or Firm* — Michael E. Zall

(57) ABSTRACT

A travel kit used for inhibiting and reducing the incidence and effect of insect bites. The kit includes a pouch for enclosing a plurality of containers therein. The pouch has a closure means to maintain the containers in the pouch and a means for removably attaching the pouch to a person. The plurality of containers includes a first container containing at least one oral tablet comprising an effective amount of niacin (vitamin B-3) or its corresponding amide for inhibiting or reducing the incidence of insect bites. A second container is provided which contains a soap composition that includes an effective antimicrobial compound that when applied to a bite area of a person's skin that has an insect bite disinfects such bite area. A third container contains a mud composition that includes an effective amount of a clay that when applied to the bite area reduces the swelling, inflammation or itching of the bite area. A fourth container is provided which contains an effective sterilizing wash composition that when applied to the bite area sterilizes the bite area and assists in reducing the swelling, inflammation or itching of the bite area. Optionally, the kit further includes a fifth container containing at least one oral tablet comprising an effective amount of an antihistamine.

10 Claims, 2 Drawing Sheets

KIT FOR INSECT BITES

FIELD OF THE INVENTION

This invention relates to a method and kit for inhibiting and/or reducing the incidence and effect of insect bites. More particularly, the method and kit of this invention can be used to inhibit mosquitoes from biting a subject and can be used to reduce swelling, inflammation and/or itching after an insect bite.

BACKGROUND OF THE INVENTION

Flying and crawling insects, including mosquitoes, ticks, flies, midges, chiggers, and fleas, often bite people. Although such insects are mostly a nuisance in North America, they can and do transmit to their bite victims more than 100 bacterial, protozoan, parasitic, and rickettsial diseases.

Mosquitoes transmit more diseases to humans than any other biting insect. Mosquitoes are the responsible for transmitting several forms of viral encephalitis, yellow fever, dengue fever, bancroftian filariasis, and epidemic polyarthritis. Malaria, which is transmitted by the bite of a mosquito, is responsible for millions of deaths annually. West Nile Virus (WNV), a deadly disease, is transmitted principally by mosquitoes, but also can be transmitted by Aedes, Anopheles, and other species.

Despite the need for an effective oral inhibitor for biting insects, no such agent has been identified thus far. The quest to develop the perfect topical insect repellent has been an ongoing scientific goal for years but has yet to be achieved. A distinction is made herein between insect repellents, which prevent biting insects from landing on a subject, and inhibitors of biting insects, which inhibit insects from biting a subject after landing.

Although a particular composition may have efficacy as both an inhibitor and a repellant of biting insects, commercially available formulations typically act as insect repellants. Commercial insect repellents may generally be characterized as involving topical application, usually are effective for limited duration, may cause severe irritation of skin or mucous membranes, may be abraded or washed off, possess a pungent odor and greasy texture, and arguably may have toxic side effects.

The effectiveness of any insect repellent is reduced by abrasion from clothing; evaporation and absorption from the skin surface; wash-off from sweat, rain, or water; a windy environment; and high ambient temperatures. Typical commercial insect repellents include DEET, i.e., N, N-diethyl-3-methylbenzamide which remains the standard of currently available insect repellents, e.g., OFF, Cutter, Repel brands. Other commercial brands are Skin-So-Soft Bath Oil (Avon Corporation), Citronella, Soybean Oil, and Eucalyptus.

There exist compositions which when orally ingested inhibit insects from biting subjects and/or reduce inflammation, swelling, redness and/or itching of the localized region of an insect bite. Such compositions may be provided in any form known in the art, but in one embodiment come in the form of a water-based solution suitable for administration with a spray bottle, for example by spraying into the mouth of a subject, followed by ingestion. Other compositions exist in forms suitable for human oral and/or external application that include one or more vitamins combined with one or more herbs to inhibit mosquitoes from biting subjects.

Such known compositions for oral and/or external application may be provided in a variety of forms, including but not limited to a dilute liquid, a concentrated liquid, a more concentrated cream, a paste or a hydratable dry composition. Other possible forms may include solutions, lotions, creams, gels, aerosol and pump sprays, and impregnated towelettes.

Thus, in general, certain known treatments are directed to minimize, inhibit and/or prevent insect bites. Other treatments are directed to treating a subject after they are bitten by an insect. Applicants' invention described and claimed herein is directed to a kit and method for both minimizing, inhibiting and/or prevent insect bites and treating a person after being bitten by an insect.

Applicants are aware of the following references:

U.S. Pat. No. 7,115,286 to Meredith describes methods and compositions to inhibit insects from biting a subject. The compositions may be administered orally, e.g., a spray delivered to the mouth. The compositions and methods are said to reduce swelling, itching, redness and/or inflammation of the local area of an insect bite. The compositions described include one or more herbs selected from the group consisting of rice bran, peppermint, barley grass, lobelia; chlorella, watercress, alfalfa and parsley and one or more vitamins selected from the group consisting of thiamin (B-1), riboflavin (B-2), niacin (B-3), pantothenic acid (B-5), pyridoxine (B-6), folic acid (B-9), cyancobalamin (B-12), choline, inositol, d-biotin, para-aminobenzoic acid, and lecithin. Administration of effective amounts of the compositions is sufficient to inhibit insects from biting and/or treat insect affected areas of a subject. In particular, there is described the oral administration of a composition containing niacin (75-300 mg) composition for the prevention of insect bites in a subject.

US Published Application No. 2006/0178368 (and U.S. Pat. No. 7,026,319) to Valletta discloses the use of niacin in a vitamin combination for the systemic treatment of itching and of pruritis. In particular, the reference describes the use of a combination of two vitamin compounds, i.e. riboflavin (also known as vitamin B2) and nicotinic acid (also referred to as niacin) or their corresponding amides, i.e. nicotinamide or niacinamide (also known as vitamin PP) for the systemic treatment of various forms of itching.

US Published Application No. 2006/0171936 to Gueniche et al. discloses a cosmetic and/or dermatological composition containing microorganisms intended for treating and/or preventing reactive sensitive skin, for example, associated with dryness of the skin. The reference teaches the use of such micro-organisms contained in an oral composition that additionally contains niacin as an active agent for treating and/or preventing reactive sensitive skin.

U.S. Pat. No. 5,888,520 and U.S. Pat. No. 6,110,475 to Toma et al. describe a composition and a method for preventing or reducing contact dermatitis. The composition contains a polysaccharide, a low molecular weight, synergistic saccharide, a solvent, and optionally an additive material. A topical triclosan composition is used as an additive material.

U.S. Pat. No. 5,702,709 to Schulz et al. describes a protective skin lotion comprising an organophilic clay including bentonite, a volatile alcoholic solvent and a cosmetically inert emollient vehicle, a thickener and water. The lotion is capable of protecting the skin from the effects of exposure to irritants and allergens, particularly those produced by toxic plants such as poison ivy.

U.S. Pat. No. 6,551,607 to Minerath et al. describes a method of sequestering skin irritants with a composition comprising modified and non-modified clays.

U.S. Pat. No. 6,248,763 to Scivoletto describes compositions for skin treatment that include nicotinamide, nicotinic acid, and nicotinic esters as active ingredients. The compositions are applied topically to the skin to treat skin conditions including acne, fine lines and age spots, itching and pain from insect bites, bee stings, fungi (including athletes foot and jock itch), flaking and/or scaly skin (including dandruff, seborrheic dermatitis, psoriasis and heat rash), and burns.

U.S. Pat. No. 6,248,343 to Jampani et al. describes the use of antimicrobial alcohol-containing compositions containing triclosan for disinfecting surfaces and providing therapeutic benefits.

U.S. Pat. No. 5,017,361 to Powell, Jr. et al. describes an allergen absorbent and blocking aerosol composition for topical application to the skin that contains a highly activated organophilic clay that blocks and absorbs the allergenic oils of toxic plants such as poison ivy and the like.

WO 2005004598 to Niinivaara et al. describes an insect repellant composition that includes water, garlic, honey, lemon juice, menthol, alcohol and other ingredients.

None of these references teach or suggest the kit or method described and claimed herein for inhibiting or reducing the incidence and effect of insect bites.

OBJECTS AND SUMMARY OF THE INVENTION

It is an object of this invention to provide a kit that contains ingredients and elements needed to both to inhibit mosquitoes from biting a subject and reduce swelling, inflammation and/or itching after an insect bite.

It is another object of this invention to provide a kit that can be easily transported on a hike, run or in ones travels that can be quickly accessed for a combination of ingredients that can be sequentially used to initially prevent insect bites and, if bitten, apply compositions that will reduce swelling, inflammation and/or itching after such insect bite.

It is a further object of this invention to provide a method for initially preventing insect bites and, if bitten, apply compositions that will reduce swelling, inflammation and/or itching after such insect bite.

All of these objects are achieved by a travel kit of this invention which is used for inhibiting and reducing the incidence and effect of insect bites. The kit comprises:

a) a pouch for enclosing a plurality of containers therein, the pouch having a closure means to maintain the containers in the pouch and a means for removably attaching the pouch to a person, the plurality of containers comprising:

b) a first container containing at least one oral tablet comprising an effective amount of niacin (vitamin B-3) or its corresponding amide for inhibiting or reducing the incidence of insect bites;

c) a second container containing a soap composition that includes an effective antimicrobial compound that when applied to a bite area of a person's skin that has an insect bite disinfects such bite area;

d) a third container containing a mud composition that includes an effective amount of a clay that when applied to the bite area reduces the swelling, inflammation or itching of the bite area; and e) a fourth container containing an effective sterilizing wash composition that when applied to the bite area sterilizes the bite area and assists in reducing the swelling, inflammation or itching of the bite area.

Optionally, the kit further includes a fifth container containing at least one oral tablet comprising an effective amount of an antihistamine.

The method of this invention includes steps for using such compositions.

BRIEF DESCRIPTION OF THE DRAWINGS

Further aspects, features and advantages of the present invention will become even more apparent with reference to the following detailed description and the accompanying drawings.

The drawings are not presented to scale but are only used to illustrate the principles of the invention. In the drawings, like reference numbers indicate like elements.

DETAILED DESCRIPTION OF THE INVENTION

Figure 2:
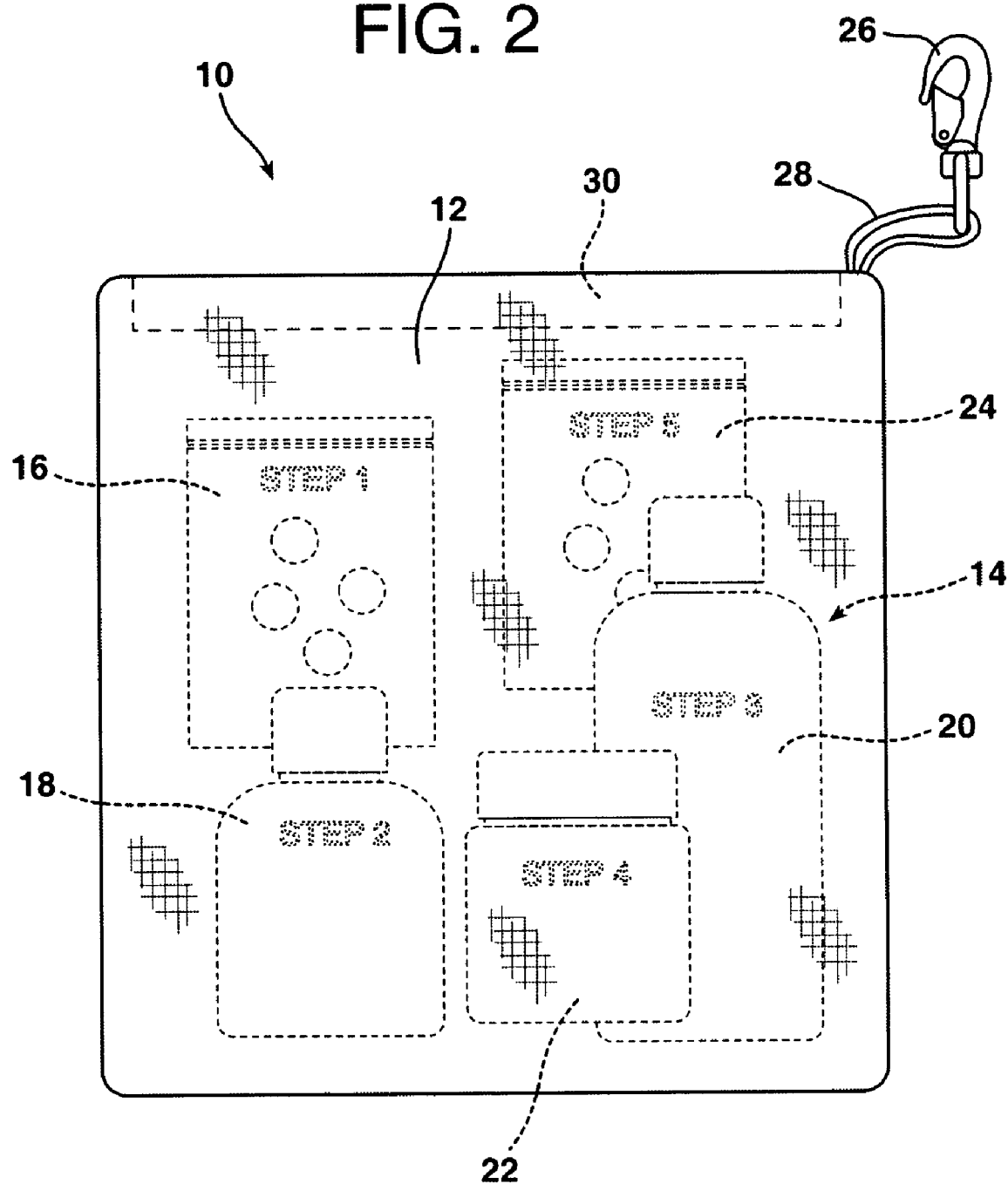
FIG. 2 is a schematic of the travel kit of this invention with the containers therein.

Referring to FIG. 2, the travel kit 10 of this invention is shown. The kit 10 is adapted to be carried by a person, for example on hikes, walks, runs or generally traveling into areas that might be infested with insects. The travel kit 10 is designed for inhibiting and reducing the incidence and effect of insect bites. The kit 10 includes a pouch 12 for enclosing therein 14 a plurality of containers 16, 18, 20, 22 and 24 each container having a specific composition used in this invention. The containers may be held in predetermined places in the interior 14 of the pouch 12 or randomly placed therein. The pouch 12 has a closure means 30, for example a VELCRO® closure means or zipper, for closing the pouch 12 to maintain the containers 16, 18, 20, 22 and 24 in the pouch 12. The pouch 12 additionally has a means 26, 28 for removably attaching the pouch 12 to a person. In the kit 10 embodiment depicted the means includes a loop 26 attached at one end to the corner of the pouch 12 and at the other end to a clip 28 that can be attached to the person's belt loop, belt, etc. This invention contemplates any type means for attaching the kit 10 to a person, e.g., VELCRO®, belt and loop, arm strap, etc.

First Container—Niacin (Vitamin B-3) Treatment

Figure 1:
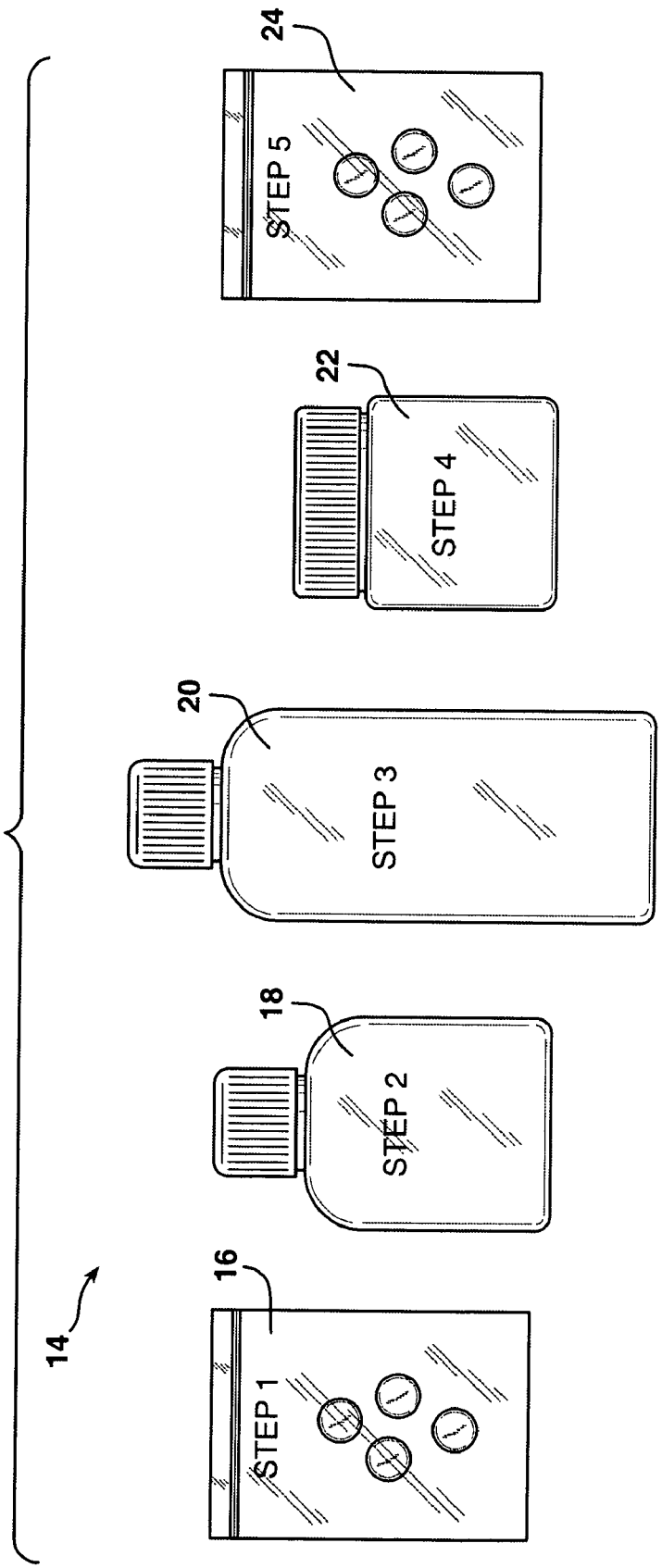
FIG. 1 is a schematic drawing of the containers used in the travel kit of this invention.

Referring to FIGS. 1-2, the kit 10 of this invention includes a first container 16 containing at least one oral tablet comprising an effective amount of niacin (vitamin B-3) or its corresponding amide for inhibiting or reducing the incidence of insect bites. In the method of this invention, the first step is orally ingesting at least one oral tablet comprising an effective amount of niacin (vitamin B-3) or its corresponding amide for inhibiting or reducing the incidence of insect bites.

As used herein, an "inhibitor" of biting insects or "biting insect inhibitor" refers to a composition that reduces the number of insect bites suffered by a subject after administration of the composition, in comparison to a control subject exposed to insects under identical circumstances without administration of the composition. It will be understood that an "inhibitor" of biting insects may or may not also repel insects, that is prevent insects from landing on a subject.

In preferred embodiments, the oral tablet used in this invention is effective to completely inhibit biting insects, i.e., the subject suffers no insect bites after administration of the composition. However, the skilled artisan will realize that efficacy of insect inhibitors may depend upon a variety of factors; such as the dosage of inhibitor administered, the length of time following administration, the body mass of the subject, the number and species of biting insects present, and environmental factors such as humidity, temperature, wind speed, sunlight or shade, etc. Ideally the oral tablet inhibits insects from biting subjects following oral administration to the subjects and provides prolonged protection of subjects against biting insects.

The oral tablets contain as an active ingredient niacin (Vitamin B-3) or its corresponding amide, i.e., niacinamide. Niacin is known to improve circulation and reduce the cholesterol level in the blood, maintain the nervous system, help metabolize protein, sugar and fat, reduce high blood pressure, increase energy through proper utilization of food, prevents pellagra, and help maintain a healthy skin, tongue and digestive system. Additionally, niacin/vitamin B3 is required for cell respiration, helps in the release of energy and metabolism of carbohydrates, fats, and proteins, proper circulation and healthy skin, functioning of the nervous system, and normal secretion of bile and stomach fluids. It is used in the synthesis of sex hormones, treating schizophrenia and other mental illnesses, and as a memory-enhancer. People report more mental alertness when this vitamin is in sufficient supply. Niacin is best taken with the B group vitamins and vitamin C.

The RDA is the minimum amount of vitamin required per day to ward off a serious deficiency of this particular nutrient. In the therapeutic use of this vitamin, the dosage is usually increased considerably, but the toxicity level must be kept in mind. Male 18 mg per day and female 13 mg per day although 100 mg is mostly used in supplementation. For use in this invention doses of from two to five times the RDA is recommended. Such levels assist in inhibiting bug bites.

Such multiples of RDA of niacin/vitamin B-3 may cause flushing by dilating the blood vessels, which can also cause the blood pressure to drop. However, these flushes are normally harmless.

The oral tablets used in this invention may also include other ingredients such as carriers, plant cellulose, dicalcium phosphate, magnesium stearate, etc. that are harmless to the effect of the niacin/vitamin B-3.

Second Container—Antibacterial Soap Treatment

Referring to FIGS. 1-2, the kit 10 of this invention includes a second container 18 containing a soap composition that includes an effective antimicrobial compound that when applied to a bite area of a person's skin that has an insect bite disinfects such bite area. Thus, in the method of this invention if an insect bites an area of the person's skin to produce a bite area the soap composition is topically applied to the bite area to thereby disinfect the bite area.

The preferred antimicrobial is triclosan, commonly known as, 2,4,4'-trichloro-2-hydroxydiphenyl ether. Triclosan may be employed from about 0.1 to about 2.0, preferably from about 0.2 to about 1.0 by weight of the soap composition.

Other antimicrobial compositions in effective amounts may be effective in this invention. These compositions include, PHOSPHOLIPID PTC, GERMALL PLUS and GERMABEN II.

In addition to the antimicrobial compositions recited above, other antimicrobials may be employed with the present invention including nisin, bis-guanides, chlorhexidine gluconate, chlorhexidine digluconate, chlorhexidine diacetate, chlorhexidine dihydrochloride, triclosan, sodium hydroxy methyl glycinate, octanoyl collagenic acid, cetyl pyridinium chloride, phenol, iodine, parachlorometaxylenol (PCMX), polymeric quaternary ammonium compounds, their combinations and the like. The antimicrobial compositions are typically added at a level of from 0.1 to about 4.0 percent by weight of the soap composition.

The soap compositions used in this invention may be in solutions, lotions, creams, gels, aerosol and pump sprays, and impregnated towelettes.

Third Container—Mud Treatment

Referring to FIGS. 1-2, the kit 10 of this invention includes a third container 20 containing a mud composition that includes an effective amount of a clay that when applied to the bite area reduces the swelling, inflammation or itching of the bite area. The mud composition is applied to the disinfected bite area to reduce the swelling, inflammation or itching of the bite area.

The mud composition acts to relieve the skin irritation caused by the insect bite. The mud preferably includes organophilic clays. The organophilic clays may be any conventional organophilic clay of commerce suitable for drug use. Such organophilic clays are well known and can be prepared from any of the clays of the smectite class that are known to swell in water and hydrophilic solvents to form viscous suspensions. Suitable clays include naturally occurring montmorillonite, bentonite, beidellite, hectorite, saponite and stevensite, their synthetically made counterparts and mixtures thereof.

The topical mud treatment used in this invention acts as an adsorbent and barrier for toxins created by the bite as well as a barrier that protects the skin from contact with irritants and allergens. The clays are dispersed in a cosmetically acceptable emollient vehicle that permits the material to be spread conveniently and evenly over the bite area. The emollient vehicle should preferably be inert with respect to the organophilic clay, i.e., it should be devoid of materials that will deactivate the adsorptive or barrier properties of the organophilic clay for allergens. The lotion should have a viscosity that permits easy spreading of the material without excessive running or dripping. To this end the lotion incorporates a swellable hydrophilic clay thickener in an aqueous-alcoholic solvent for the emollient vehicle. The concentration of the thickener is adjusted to provide the proper viscosity.

The organophilic clay is present in the protective lotion in the proportion of 3.0-10.0% by, weight, preferably 4.0-6.0% by weight and more preferably about 5.0% by weight.

The lotion of the invention comprises a cosmetically acceptable emollient, liquid at room temperature and soluble in the alcoholic solvent, that does not react with the organophilic clay to deactivate its barrier properties and adsorptive capacity. The volatile alcohol solvent used in the allergen protective lotion of the invention can be any cosmetically acceptable volatile alcohol. Typically, the volatile alcohol will be ethanol or isopropyl alcohol.

A thickener may be used in the mud composition of this invention. An example of such a thickener is an organic polymeric thickener such as is conventionally used in aqueous pharmaceutical solutions. Such thickeners include hydroxyethyl cellulose, hydroxypropyl cellulose, hydroxypropyl methylcellulose, methylcellulose, carboxymethylcellulose sodium, poly(vinyl alcohol), poly(vinylpyrrolidone), poly (acrylic acid) sodium salt, and the like. The thickener may be present in the mud composition of the invention in an amount sufficient to provide a viscosity suitable for convenient application and spreading on the skin. The skilled practitioner will also recognize that, because different thickeners have different effects on the viscosity of aqueous media, the amount of each thickener used will be adjusted to give an appropriate viscosity to the lotion.

The mud composition used in this invention is spread over the portion of the skin to provide a generally uniform layer of the organophilic clay adsorbent over the bite area. After application any volatile alcohol component of the mud composition evaporates and the emollient vehicle is largely absorbed into the skin, leaving thereon a coating of the organophilic clay which provides a barrier against environmental allergens and irritants and reduces the swelling, inflammation or itching of the bite area.

A preferred commercially available mud composition is Queen Helen Mud Pack Masque, although numerous others are known and can be useful in this invention. The Queen Helen Mud Pack Masque contains distilled water, kaolin, bentonite, glycerin, zinc oxide, propylene glycol, iron oxides, fragrance, and methylparaben.

Fourth Container—Wash Treatment

Referring to FIGS. 1-2, the kit 10 of this invention includes a fourth container 22 containing an effective sterilizing wash composition that when applied to the bite area sterilizes the bite area and assists in reducing the swelling, inflammation or itching of the bite area. The wash composition is topically applied to the mud treated bite area to sterilize the bite area and assist in reducing the swelling, inflammation or itching of the bite area. Optionally or additionally, it may also be applied after treatment of the bite area with the soap composition and before treatment with the mud composition.

The wash composition can include any number of compounds and compositions such as distilled water, Witch Hazel, peroxide, and mixtures thereof.

Fifth Container—Pain/Antihistamine Relief Treatment

Referring to FIGS. 1-2, the kit 10 of this invention may further include a fifth container 24 containing at least one oral tablet comprising an effective amount of an antihistamine, pain reliever or other type medication that can be used to counter any physical effects from the bug bite.

The invention has been described with reference to various specific and illustrative aspects of the present invention and techniques. However, it should be understood that many variations and modifications may be made while remaining within the spirit and scope of the invention. Many alternatives, modifications and variations will be apparent to those skilled in the art in light of the foregoing description. Accordingly, this invention is intended to embrace all such alternatives, modifications, and variations that fall within the spirit and scope of the appended claims.

What is claimed:

1. A travel kit for a person for inhibiting and reducing the incidence and effect of insect bites,
   the kit consisting essentially of:
   a) a pouch for enclosing a plurality of containers therein, the pouch having a closure means to maintain the containers in the pouch and a means for removably attaching the pouch to a person, the plurality of containers comprising:
   b) a first container containing at least one oral tablet consisting of an effective amount of niacin (vitamin B-3) or its corresponding amide as the only active ingredient for inhibiting or reducing the incidence of insect bites;
   c) a second container containing a soap composition that includes an effective antimicrobial compound that when applied to a bite area of a person's skin that has an insect bite, disinfects such bite area;
   d) a third container containing a mud composition that includes an effective amount of a clay that when applied to the bite area reduces the swelling, inflammation or itching of the bite area; and
   e) a fourth container containing an effective sterilizing wash composition that when applied to the bite area sterilizes the bite area and assists in reducing the swelling, inflammation or itching of the bite area; and
   f) directions consisting essentially of:
      1) orally ingesting the at least one oral tablet from the first container for inhibiting or reducing the incidence of insect bites, and then if an insect bites an area of the person's skin:
      2) applying to the bite area the soap composition from the second container to disinfect the bite area; and then
      3) applying to the disinfected bite area the mud composition from the third container to reduce the swelling, inflammation or itching of the bite area; and then
      4) applying to the mud treated bite area the sterilizing wash composition from the fourth container to sterilize the bite area and assist in reducing the swelling, inflammation or itching of the bite area.

2. The travel kit of claim 1, further including a fifth container containing at least one oral tablet that includes an effective amount of an antihistamine and the directions include orally ingesting the at least one oral tablet having an effective amount of an antihistamine from the fifth container after the insect bite.

3. The travel kit of claim 1, wherein the antimicrobial, composition is triclosan.

4. The travel kit of claim 1, wherein the clay is selected from the group consisting of bentonite, montmorillonite, beidelite, hectorite, saponite, stevensite and mixtures thereof.

5. The travel kit of claim 1, wherein the sterilizing wash composition contains distilled water, Witch Hazel, peroxide or mixtures thereof.

6. A method for inhibiting and reducing the incidence and effect of insect bites for a person, consisting essentially of:
   a) orally ingesting at least one oral tablet consisting of an effective amount of niacin (vitamin B-3) or its corresponding amide as the only active ingredient for inhibiting or reducing the incidence of insect bites; and then if an insect bites an area of the person's skin to produce a bite area;
   b) applying to the bite area a soap composition that includes an effective antimicrobial compound that when applied disinfects the bite area; and then
   c) applying to the disinfected bite area a mud composition that includes an effective amount of a clay that when applied to the bite area reduces the swelling, inflammation or itching of the bite area; and then
   d) applying to the mud treated bite area an effective sterilizing wash composition that when applied to the bite area sterilizes the bite area and assists in reducing the swelling, inflammation or itching of the bite area.

7. The method of claim 1, further including after an insect bites an area of the person's skin to produce a bite area, orally ingesting at least one oral tablet having an effective amount of an antihistamine.

8. The method of claim 6, wherein the antimicrobial composition is triclosan.

9. The method of claim 6, wherein the clay is selected from the group consisting of bentonite, montmorillonite, beidelite, hectorite, saponite, stevensite and mixtures thereof.

10. The method of claim 6, wherein the sterilizing wash composition contains distilled water, a Witch Hazel or mixtures thereof.

* * * * *